(12) United States Patent
Overes et al.

(10) Patent No.: US 9,089,436 B2
(45) Date of Patent: Jul. 28, 2015

(54) VISCO-ELASTIC FACET JOINT IMPLANT

(75) Inventors: Thomas Overes, Langendorf (CH); Beat Lechmann, Grenchen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 608 days.

(21) Appl. No.: 12/619,335

(22) Filed: Nov. 16, 2009

(65) Prior Publication Data
US 2010/0131008 A1 May 27, 2010

Related U.S. Application Data

(60) Provisional application No. 61/117,622, filed on Nov. 25, 2008.

(51) Int. Cl.
| A61B 17/70 | (2006.01) |
| A61F 2/44 | (2006.01) |
| A61F 2/30 | (2006.01) |

(52) U.S. Cl.
CPC ........... *A61F 2/4405* (2013.01); *A61B 17/7062* (2013.01); *A61B 17/7064* (2013.01); *A61F 2002/3092* (2013.01); *A61F 2002/30578* (2013.01); *A61F 2002/449* (2013.01)

(58) Field of Classification Search
CPC ........... A61B 17/7062; A61B 17/7064; A61B 17/7067
USPC .................................................. 606/246–279
See application file for complete search history.

(56) References Cited

U.S. PATENT DOCUMENTS

| 4,502,161 | A | 3/1985 | Wall | |
| 5,879,396 | A | 3/1999 | Walston et al. | |
| RE36,758 | E | 6/2000 | Fitz | |
| 6,132,464 | A | 10/2000 | Martin | |
| 6,419,703 | B1 | 7/2002 | Fallin et al. | |
| 6,440,169 | B1 | 8/2002 | Elberg et al. | ............... 623/17.16 |
| 6,565,605 | B2 | 5/2003 | Goble et al. | |
| 6,579,319 | B2 | 6/2003 | Goble et al. | |
| 6,610,091 | B1 | 8/2003 | Reiley | |
| 6,669,729 | B2 | 12/2003 | Chin | |

(Continued)

FOREIGN PATENT DOCUMENTS

| DE | 10135771 | 2/2003 |
| EP | 0767637 | 4/1997 |

(Continued)

OTHER PUBLICATIONS

PCT: International Search Report & Written Opinion.

*Primary Examiner* — Ellen C Hammond
*Assistant Examiner* — Christina Negrellirodrigue
(74) *Attorney, Agent, or Firm* — Meunier Carlin & Curfman LLC (57) ABSTRACT

A visco-elastic facet joint implant for insertion into a facet joint between an inferior facet formed on a superior vertebral body and a superior facet formed on an inferior vertebral body. The facet implant includes a visco-elastic implant element molded into an anatomically fitted shape to optimally fit between the facet joint and one or more bone fixation elements to secure the visco-elastic implant element to the superior and/or inferior vertebral bodies. In use, the visco-elastic facet joint implant includes a first end for engaging the superior vertebral body, a middle portion for passing through the facet joint and an optional second end for engaging the inferior vertebral body.

19 Claims, 6 Drawing Sheets

(56) References Cited

U.S. PATENT DOCUMENTS

| | | |
|---|---|---|
| 6,811,567 B2 | 11/2004 | Reiley |
| 6,902,580 B2 | 6/2005 | Fallin et al. |
| 6,949,123 B2 | 9/2005 | Reiley |
| 6,966,930 B2 | 11/2005 | Arnin et al. ............... 623/17.11 |
| 6,974,478 B2 | 12/2005 | Reiley et al. |
| 7,011,685 B2 | 3/2006 | Arnin et al. |
| 7,041,136 B2 | 5/2006 | Goble et al. |
| 7,051,451 B2 | 5/2006 | Augostino et al. |
| 7,074,237 B2 | 7/2006 | Goble et al. |
| 7,074,238 B2 | 7/2006 | Stinson et al. |
| 7,083,622 B2 | 8/2006 | Simonson |
| 7,087,084 B2 | 8/2006 | Reiley |
| 7,090,698 B2 | 8/2006 | Goble et al. |
| 7,371,238 B2 | 5/2008 | Soboleski et al. |
| 7,708,760 B2 | 5/2010 | Parsons ........................ 606/247 |
| 8,128,660 B2 * | 3/2012 | Mitchell et al. ............... 606/247 |
| 2004/0006343 A1 * | 1/2004 | Sevrain ........................ 606/61 |
| 2004/0127989 A1 | 7/2004 | Dooris et al. |
| 2004/0158245 A1 | 8/2004 | Chin |
| 2005/0043797 A1 | 2/2005 | Lee |
| 2005/0049705 A1 | 3/2005 | Hale et al. |
| 2005/0055096 A1 | 3/2005 | Serhan et al. |
| 2005/0131409 A1 | 6/2005 | Chervitz et al. |
| 2005/0143818 A1 | 6/2005 | Yuan et al. |
| 2005/0177240 A1 | 8/2005 | Blain |
| 2005/0203512 A1 | 9/2005 | Hawkins et al. |
| 2005/0261770 A1 | 11/2005 | Kuiper et al. |
| 2006/0004449 A1 | 1/2006 | Goble et al. |
| 2006/0004451 A1 | 1/2006 | Goble et al. |
| 2006/0041311 A1 | 2/2006 | McLeer |
| 2006/0084976 A1 | 4/2006 | Borgstrom et al. |
| 2006/0084991 A1 | 4/2006 | Borgstrom et al. |
| 2006/0100707 A1 | 5/2006 | Stinson et al. |
| 2006/0111780 A1 | 5/2006 | Petersen |
| 2006/0111781 A1 | 5/2006 | Petersen |
| 2006/0129239 A1 | 6/2006 | Kwak |
| 2006/0142759 A1 | 6/2006 | Arnin et al. |
| 2006/0149229 A1 | 7/2006 | Kwak et al. |
| 2006/0149373 A1 | 7/2006 | Winslow et al. |
| 2006/0149374 A1 | 7/2006 | Winslow et al. |
| 2006/0149383 A1 | 7/2006 | Arnin et al. |
| 2006/0184180 A1 | 8/2006 | Augostino et al. |
| 2006/0241597 A1 | 10/2006 | Mitchell et al. |
| 2006/0241758 A1 | 10/2006 | Peterman et al. |
| 2007/0055373 A1 | 3/2007 | Hudgins et al. |
| 2007/0083266 A1 | 4/2007 | Lang |
| 2007/0135814 A1 | 6/2007 | Farris ........................ 606/61 |
| 2007/0179617 A1 | 8/2007 | Brown et al. |
| 2007/0265626 A1 | 11/2007 | Seme ........................ 606/61 |
| 2007/0265706 A1 | 11/2007 | Reiley |
| 2007/0276497 A1 | 11/2007 | Anderson ................ 623/17.12 |
| 2008/0161833 A1 | 7/2008 | Ray |
| 2008/0177311 A1 | 7/2008 | Winslow et al. ............... 606/248 |
| 2009/0248081 A1 * | 10/2009 | LeHuec et al. ............... 606/263 |
| 2011/0106163 A1 * | 5/2011 | Hochschuler et al. ......... 606/264 |

FOREIGN PATENT DOCUMENTS

| | | | |
|---|---|---|---|
| EP | 1 437 101 | 7/2004 | ............... A61F 2/44 |
| FR | 2832054 | 5/2003 | |
| WO | WO0053126 | 9/2000 | |
| WO | WO2004014261 | 2/2004 | |
| WO | WO2004026170 | 4/2004 | |
| WO | WO2005020850 | 3/2005 | |
| WO | WO2005030087 | 4/2005 | |
| WO | WO2005037149 | 4/2005 | |
| WO | WO2005044152 | 5/2005 | |
| WO | WO2005072661 | 8/2005 | |
| WO | WO2005079426 | 9/2005 | |
| WO | WO2005086776 | 9/2005 | |
| WO | WO2005112835 | 12/2005 | |
| WO | WO200623671 | 2/2006 | |
| WO | WO2006039260 | 4/2006 | |
| WO | WO200667790 | 6/2006 | |
| WO | WO2006073573 | 7/2006 | |
| WO | WO2006073593 | 7/2006 | |
| WO | WO 2009/006455 | 1/2009 | ............. A61B 17/70 |

* cited by examiner

VISCO-ELASTIC FACET JOINT IMPLANT

CROSS-REFERENCE TO RELATED APPLICATIONS

This application claims the benefit of U.S. Provisional Application No. 61/117,622 filed on Nov. 25, 2008, entitled "FACET JOINT AUGMENTATION WITH VISCO-ELASTIC INTER-ARTICULAR SPACER," the contents of which is incorporated in its entirety by reference herein.

BACKGROUND OF THE INVENTION

Flexible motion segments of the human spine include at least a pair of vertebrae, each with a vertebral body, an intervertebral disc located between the vertebral bodies to provide a cushion and secure the vertebral bodies together, and a pair of facet joints, which are small stabilizing joints located posteriorly relative the vertebral bodies. The facet joints and the intervertebral disc, with the help of various ligamentation, function as a three joint entity to permit motion, but prevent excessive motion, over-twisting, or toppling over of the spine.

Each facet joint includes two articulating processes and a joint capsule. The surfaces of the facet joints are covered by an articular cartilage. The superior half of each facet joint is attached to the posterior portion of each vertebral body, on either side of the spinous process, and extends inferiorly. The inferior half of each facet joint extends superiorly from the inferior vertebral body to interact with the inferiorly extending, superior half of the facet joint.

Facet joints are in almost constant motion with the spine and may wear out or become degenerated due to aging, trauma, typical use and other factors. Facet joint degeneration or disruption is often preceded by instabilities or other degeneration of the anterior spine, often causing an overload on the facet joint. When facet joints become worn or torn, the cartilage may become thin or disappear and there may be a reaction of the bone of the joint underneath that produces overgrowth of bone spurs and an enlargement of the joints. The joint is then said to have arthritic changes, or osteoarthritis, that can produce considerable back pain during motion. This condition is also referred to as facet joint disease or facet joint syndrome.

Additionally, inflammatory reactions may occur when the cartilaginous surfaces of the facets become degraded or fissured, thereby leading to direct bone-on-bone contact and resulting in pain. Conventionally, patients have undergone interbody fusion surgery to alleviate such pain, in which the intervertebral disc space is removed and a spacer is inserted therein through which fusion of the adjacent vertebral bodies occurs, which by its nature is irreversible, non-motion-preservable, and oftentimes invasive. Commercially available and clinically tested solutions for facet joint replacement mostly feature dampening elements that are placed between pedicle screws. However, due to the limited bone stock a pedicle is capable of supplying, such interventions can result in follow-up surgery after further degeneration (the pedicles are needed for posterior stabilization in the case of subsequent fusion surgery). Furthermore, such interventions almost always include complete laminectomies, after which posterior fusion using trans-laminar techniques is extremely limited.

It is desirable to develop an implant for insertion into the facet joints between adjacent superior and inferior vertebral bodies to alleviate pressure on the painful articulating areas resulting from degenerating facet joints that may be implemented in a minimally invasive and bone sparing manner, and to provide the patient with pain-free mobility.

BRIEF SUMMARY OF THE INVENTION

The present invention relates to a visco-elastic facet implant for insertion into a facet joint between an inferior facet formed on a superior vertebral body and a superior facet formed on an inferior vertebral body.

In one exemplary embodiment, the facet implant includes a first implant element including a first end for engaging the superior vertebral body via one or more bone fixation elements, a middle portion for passing through the facet joint and a second end. The implant element is manufactured from an elongated strip of visco-elastic material that is preferably adaptable to an anatomy of the vertebral bodies. More preferably, the visco-elastic material is selected from one of a polycarbonate-urethane or silicon and the visco-elastic implant element may be injection molded into a flexible shape.

The second end of the implant element may be secured to the inferior vertebral body via one or more fixation elements. Alternatively, the middle portion and the second end of the implant element may be in the form of a cap for surrounding at least a portion of the inferior facet formed on the superior vertebral body (e.g., the superior half of the facet joint). The middle portion of the implant element may include an extension for passing through the facet joint so that the implant element may be disposed along side the facet joint in an implanted position.

In another exemplary embodiment, the facet implant is sized and adapted for insertion into first and second facet joints between a superior vertebral body and an inferior vertebral body wherein the first and second facet joints are located on opposite sides of a spinous process. The facet implant includes a first inferior end for engaging the inferior vertebral body, a middle portion for passing through the first facet joint, a first superior end for engaging the superior vertebral body, an intermediate superior portion for passing through an interspinous space, a second superior end for engaging the superior vertebral body on the opposite side of the spinous process, a second middle portion for passing through the second facet joint, and a second inferior end for engaging the inferior vertebral body. The implant is manufactured from an elongated strip of visco-elastic material that is preferably adaptable to an anatomy of the vertebral bodies. Preferably the visco-elastic material is selected from one of a polycarbonate-urethane or silicon and the visco-elastic implant may be injection molded into a flexible shape.

The implant or implant elements may include one or more eyelets for receiving one or more bone fixation elements for securing the implant or implant elements to the superior and/or vertebral bodies. More preferably, the implant or implant elements are secured to a laminar arch of the superior and/or inferior vertebral bodies.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the facet joint augmentation system and associated method of use of the present invention, drawings of the preferred embodiments are shown. It should be understood, however, that the application is not limited to the precise arrangement, structures, features, embodiments, and aspects shown, and that the arrangements, structures, features, embodiments and aspects shown may be used singularly or in combination with other arrangements, structures, features, aspects and embodiments. In the drawings.

DETAILED DESCRIPTION OF THE INVENTION

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the facet joint augmentation system and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. Preferred embodiments of the present invention are directed to a facet joint augmentation system or implant 10, 100, 200, 300 (10-300) for insertion between one or more facet joints $FJ_1$, $FJ_2$ between adjacent superior and inferior vertebral bodies V and an accompanying surgical method for inserting the facet joint implant 10-300 into the facet joints $FJ_1$, $FJ_2$. It should be appreciated that while the facet joint implant 10-300 of the present application will be described as and may generally be used for insertion into the facet joints $FJ_1$, $FJ_2$ in a patient's spine (for example, in the lumbar, thoracic or cervical regions), one of ordinary skill in the art will understand that the implant 10-300, as well as the components thereof, may be used in other parts of the body including, for example, for insertion into the interspinous space (FIGS. 6A and 6B), the knee, hip, shoulder, finger, joints, long bones or bones in the hand, face, feet, etc.

Figure 1A:
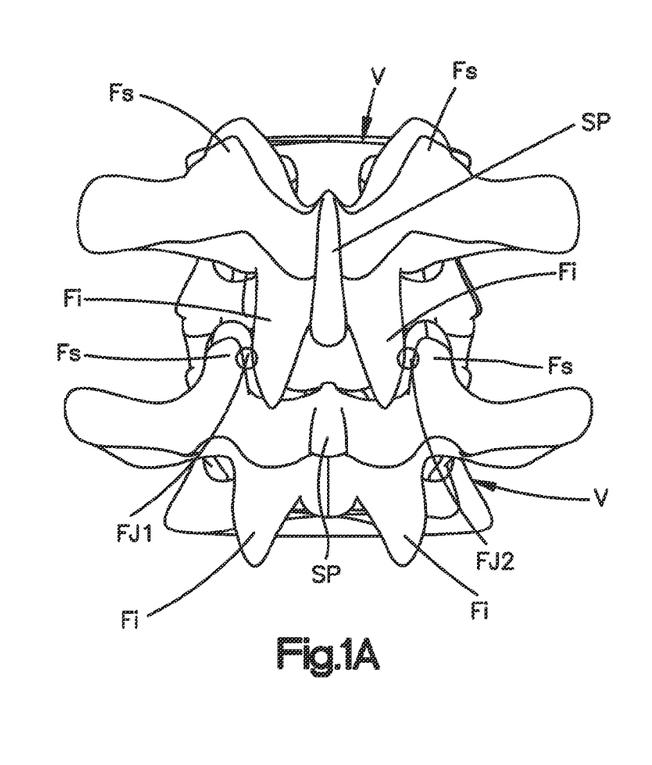
FIG. 1A illustrates a posterior elevational view of a patient's spine.
Figure 1B:
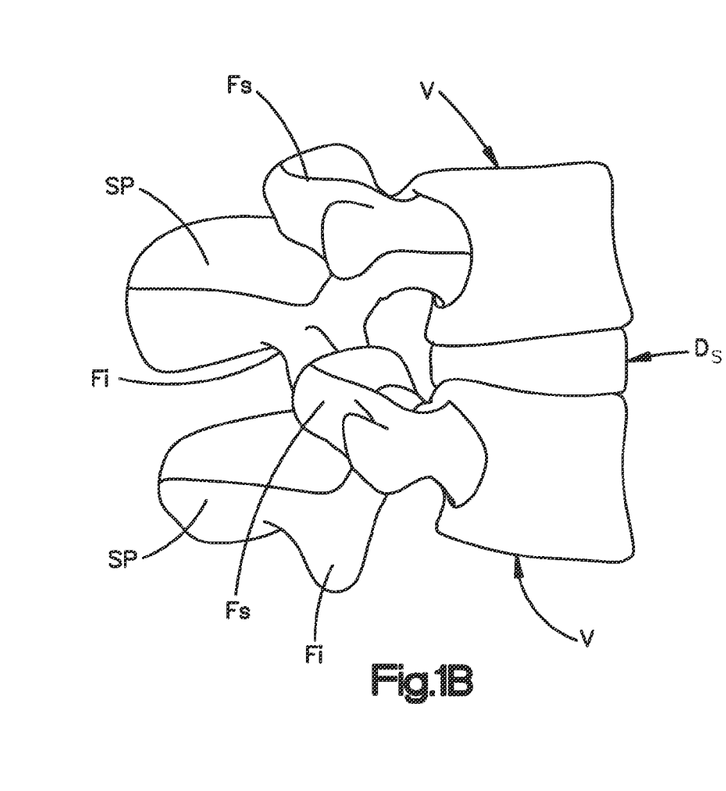
FIG. 1B illustrates a side elevational view of the patient's spine shown in FIG. 1A.

Referring to FIGS. 1A and 1B, two exemplary vertebral bodies V in the lumbar region of a patient's spine are shown. The vertebral bodies V each include a pair of superior articular facets $F_S$ and a pair of inferior articular facets $F_i$ on either side of the spinous process SP. The inferior facet $F_i$ on the superior vertebral body V and the superior facet $F_S$ on the inferior vertebral body V are movably interconnected via a joint capsule or facet joint space $FJ_1$, $FJ_2$ that guide and limit motion of the spinal segment. The vertebral bodies V shown in FIGS. 1A and 1B include a first facet joint $FJ_1$ positioned to a left-side of the spinous process SP and a second facet joint $FJ_2$ positioned to a right-side of the spinous process SP.

The facet joints $FJ_1$, $FJ_2$ guide and facilitate movement between the superior and inferior vertebral bodies V. As a result of natural or traumatic degeneration of the spine, the facet joints $FJ_1$, $FJ_2$ may be affected. For example, an inflammatory reaction may occur when the cartilaginous surfaces of the facet joints $FJ_1$, $FJ_2$ are degraded, which may lead to direct contact between the inferior facet $F_i$ formed on the superior vertebral body V and the superior facet $F_S$ formed on the inferior vertebral body V, resulting in pain in the facet joints $FJ_1$, $FJ_2$.

Augmentation of the facet joints $FJ_1$, $FJ_2$ to alleviate pressure on the painful area may be achieved via the insertion of a facet joint implant 10-300 between the inferior facet $F_i$ formed on the superior vertebral body V and the superior facet $F_S$ formed on the inferior vertebral body V. The facet joint implant 10-300 preferably allows for the treatment of the facet joints $FJ_1$, $FJ_2$, permitting preservation of mobility and/or stabilization while enabling the pedicles to remain intact. Augmentation of the facet joints $FJ_1$, $FJ_2$ is preferably achieved via the insertion of two facet joint implants 10-300, one for each of the facet joints $FJ_1$, $FJ_2$. In addition, the facet joint implant 10-300 may be inserted with or without insertion of an interbody spacer within the intervertebral disk space $D_S$ between the adjacent vertebral bodies V. Accordingly, the facet joint implant 10-300 may be used as a stand alone device in the case of isolated facet pain or can be combined with a constrained or semi-constrained total disc replacement (TDR) implant due in part to the unconstrained character of the implant 10-300, which generally forces no motion patterns to the TDR.

Figure 2:
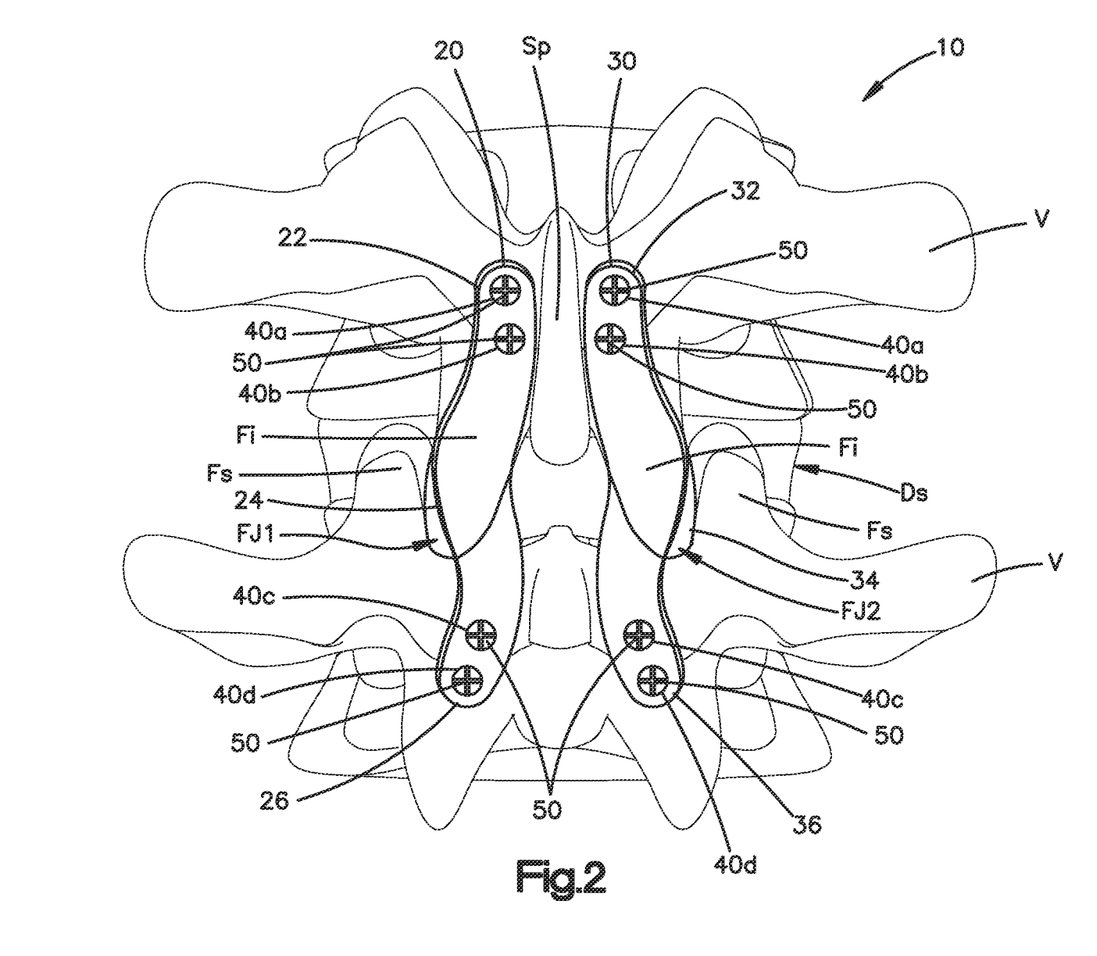
FIG. 2 illustrates a posterior elevational view of a first preferred embodiment of a facet augmentation implant according to the present invention.

Referring to FIG. 2, the first embodiment of the facet joint implant 10 includes first and second implant elements 20, 30. The first and second implant elements 20, 30 are preferably made of a substantially flat, elongated anatomical strip of visco-elastic material, such as polycarbonate-urethane (PCU) or silicon that is adaptable to the posterior anatomy of the adjacent superior and inferior vertebral bodies V. The first and second implant elements 20, 30 are preferably molded into anatomically fitted forms which are shaped to optimally fit between the facet joints $FJ_1$, $FJ_2$. Alternatively, as will be appreciated by one of ordinary skill in the art, the first and second implant elements 20, 30 may be completely flat and flexible.

The first and second implant elements 20, 30 each include a first end 22, 32 for engaging the superior vertebral body V, a middle portion 24, 34 which passes through the facet joint $FJ_1$, $FJ_2$, respectively, and a second end 26, 36 for engaging the inferior vertebral body V. The first and second implant elements 20, 30 preferably engage the superior and inferior vertebral bodies V adjacent to or with the spinous process SP. More preferably, the first and second implant elements 20, 30 preferably engage the superior and inferior vertebral bodies V in the laminar arch and/or through the pedicles.

Each of first and second implant elements 20, 30 preferably includes a plurality of eyelets 40 for receiving a plurality of bone fixation elements 50 for securing the first and second implant elements 20, 30 to the adjacent vertebral bodies V. The bone fixation elements 50 are preferably bone screws.

Alternatively, as will be appreciated by one of ordinary skill in the art, the bone fixation elements 50 may be any now known or hereafter developed bone engaging mechanism including rivets, riveting nails, pins such as poly-lactide pins, short bone screws such as cranial maxillofacial (CMF) screws, sutures such as strong, flexible surgical sutures (e.g., meniscal repair sutures), or any combination thereof. The use of sutures as the bone fixation elements 50 particularly enables revision surgeries or repositioning or subsequent removal of the facet joint implant 10 to occur in a minimally invasive fashion.

The first implant element 20 preferably includes first and second eyelets 40a, 40b for securing the first end 22 of the first implant element 20 to the superior vertebral body V and third and fourth eyelets 40c, 40d for securing the second end 26 of the first implant element 20 to the inferior vertebral body V. Similarly, the second implant element 30 preferably includes first and second eyelets 40a, 40b for securing the first end 32 of the second implant element 30 to the superior vertebral body V and third and fourth eyelets 40c, 40d for securing the second end 36 to the inferior vertebral body V. As will be appreciated by one of ordinary skill in the art based on a reading the present disclosure, any number of eyelets 40 may be used to secure the first and second implant elements 20, 30 to the adjacent vertebral bodies V including, for example, two, three, five or more.

The eyelets 40 are preferably are manufactured from metal. Alternatively, as will be appreciated by one of ordinary skill in the art, the eyelets 40 may be manufactured from any other now or hereafter developed rigid material. The eyelets 40 are preferably injection molded into the first and second implant elements 20, 30 and preferably function as attachment point inserts for the bone fixation elements 50. The eyelets 40 may be interiorly threaded for threadably engaging an exterior thread formed on a head portion of the bone fixation elements 50. Alternatively, as will be appreciated by one of ordinary skill in the art, the eyelets 40 may include exterior threading or no threading at all.

Alternatively, as will be appreciated by one of ordinary skill in the art, the eyelets 40 may be completely eliminated from the first and second implant elements 20, 30 and the bone fixation elements 50 may be threaded, drilled, or punched directly through the visco-elastic material of the first and second implant elements 20, 30. Alternatively, the eyelets 40 may be replaced with preformed holes.

In operation, a bilateral pair of incisions or a single posterior incision is preferably made in a patient and the patient's existing facet joint capsules are removed. Any osteophites and superflucious cartilage that are present are then removed and the facet joint spaces $FJ_1$, $FJ_2$ are cleaned and washed out. While this operation occurs, care is preferably taken to limit bleeding as much as possible, as blood tends to provoke fusion across the facet joints $FJ_1$, $FJ_2$. The first and second implant elements 20, 30 of the first facet joint implant 10 are preferably inserted between the facet joint spaces $FJ_1$, $FJ_2$ and secured in a desirable position by implanting the bone fixation elements 50 through the first and second implant elements 20, 30, more preferably through the eyelets 40, and into the superior and inferior vertebral bodies V.

A drilling template may be utilized to ease the insertion of the bone fixation elements 50 through the eyelets 40, particularly when bone screws, rivets, or pins are utilized as the bone fixation elements 50. When the bone fixation elements 50 are sutures, the sutures can be anchored directly into the bone or may be looped and tied around the bony structures of the posterior spine.

Once secured into place, the visco-elastic nature of the facet joint implant 10 allows the facet joints $FJ_1$, $FJ_2$ to maintain their mobility while providing a cushion between the superior and inferior articulating surfaces, resulting in a reduction in the pressure experienced by the articulation surfaces, and a reduction or elimination of pain. In addition, the implantation of the facet joint implant 10 preferably enables the interspinous ligament to be spared from the bone fixation elements 50.

Figure 3:
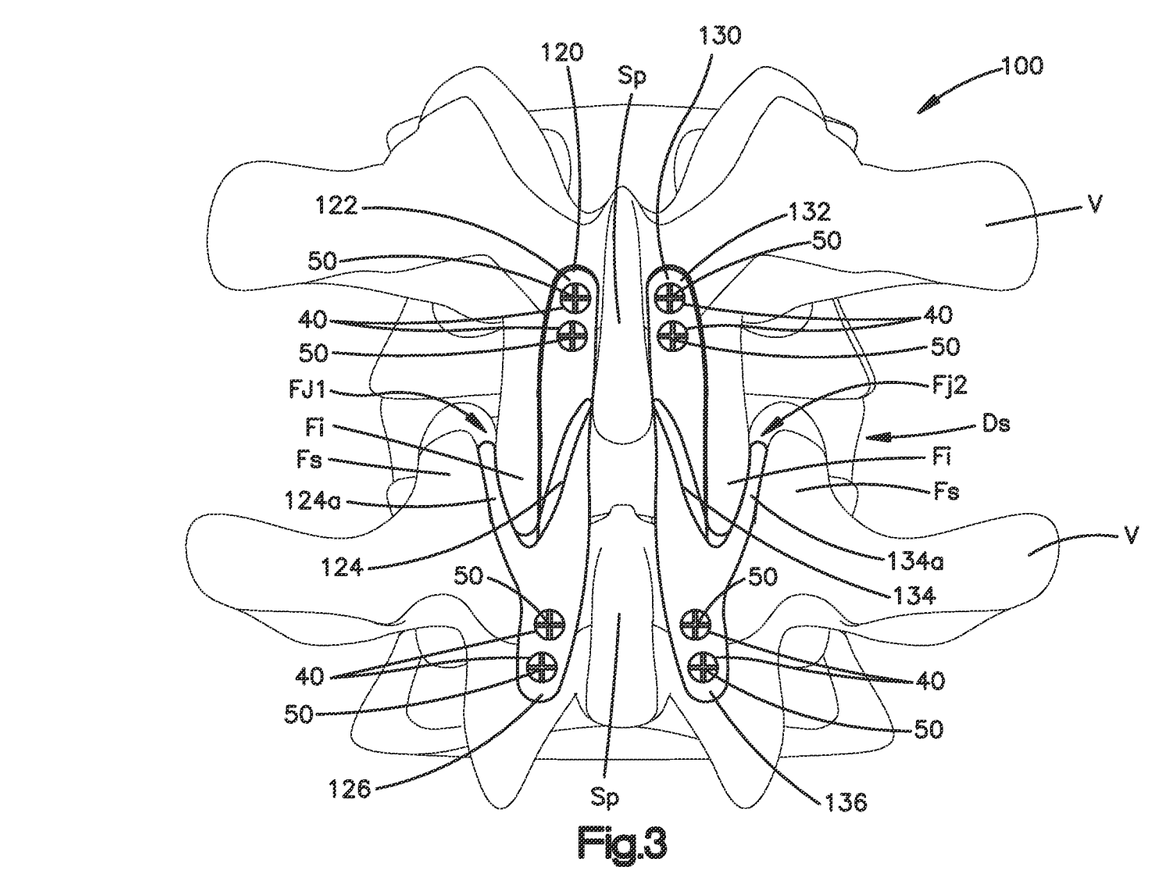
FIG. 3 illustrates a posterior elevational view of a second preferred embodiment of a facet augmentation implant according to the present invention.

Referring to FIG. 3, a second embodiment of the facet joint implant 100 includes first and second implant elements 120, 130. The second preferred embodiment of the facet joint implant 100 is similar to the first preferred embodiment of the facet joint implant 10 except in the second preferred embodiment of the facet joint implant 100, the first and second implant elements 120, 130 each include a middle portion 124, 134 which includes an extension or arm 124a, 134a for interposition between the facet joint spaces $FJ_1$, $FJ_2$, as will be described in greater detail below.

The first and second implant elements 120, 130 are preferably made of a substantially flat, elongated anatomical strip of visco-elastic material, such as polycarbonate-urethane (PCU) or silicon that is adaptable to the posterior anatomy of the adjacent superior and inferior vertebral bodies V. The first and second implant elements 120, 130 are preferably molded into anatomically fitted forms which are shaped to optimally fit between the facet joints $FJ_1$, $FJ_2$. Alternatively, as will be appreciated by one of ordinary skill in the art, the first and second implant elements 120, 130 may be completely flat and flexible.

The first and second implant elements 120, 130 each include a first end 122, 132 for engaging the superior vertebral body V, a middle portion 124, 134 incorporating an extension or arms 124a, 134a, respectively, for interposition between the facet joints $FJ_1$, $FJ_2$ and a second end 126, 136 for engaging the inferior vertebral body V. Similar to the first preferred embodiment, the second preferred embodiment of the facet joint implant 100 may include a plurality of eyelets 40 for receiving a plurality of bone fixation elements 50 for coupling the first and second ends of the first and second implant elements 120, 130 to the adjacent superior and inferior vertebral bodies V.

The middle portion 124, 134 includes an extension or arm 124a, 134a so that in use the first and second implant elements 120, 130 may be disposed along one side of the superior and inferior facets $F_i$, $F_S$. For example, as illustrated in FIG. 3, the first and second implant elements 120, 130 may extend entirely between the superior and inferior facets $F_i$, $F_S$ and the spinous process SP. That is, the first and second implant element 120, 130 do not extend between the facet joints $FJ_1$, $FJ_2$. Rather, the extension or arm 124a, 134a projecting from the middle portion 124, 134 of the first and second implant elements 120, 130 is disposed between the facet joints $FJ_1$, $FJ_2$.

In operation, a bilateral pair of incisions or a single posterior incision is preferably made in a patient and the facet joint capsules are removed. Any osteophites and superflucious cartilage that are present are then removed and the facet joint spaces $FJ_1$, $FJ_2$ are cleaned and washed out. While this operation occurs, care is preferably taken to limit bleeding as much as possible, as blood tends to provoke fusion across the facet joints $FJ_1$, $FJ_2$. The first and second implant elements 120, 130 are implanted with the extension or arm 124a, 134a inserted between the facet joint spaces $FJ_1$, $FJ_2$. The first and second implant elements 120, 130 are secured in a desirable position by implanting the bone fixation elements 50 through the first and second implant elements 120, 130 and into the adjacent vertebral bodies V, preferably in the laminar arch and/or through the pedicles. The implantation of the facet joint implants 100 preferably enables the interspinous ligament to be spared from the bone fixation elements 50.

Figure 4:
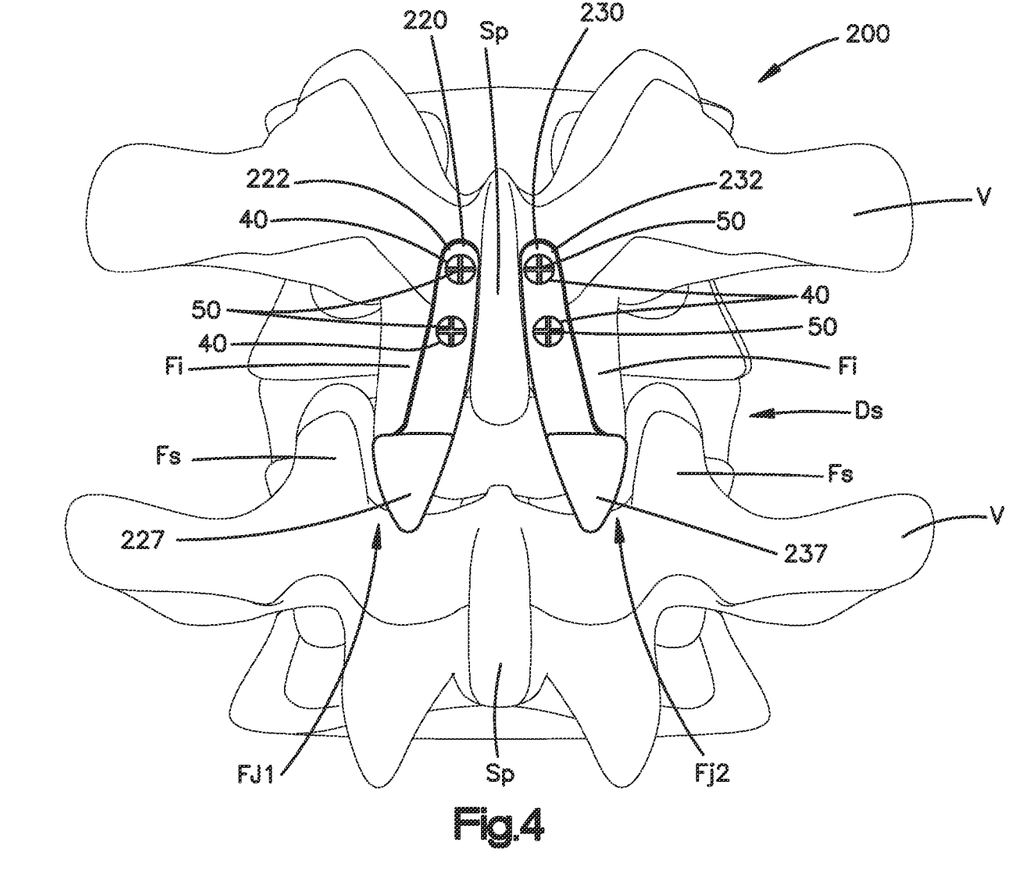
FIG. 4 illustrates a posterior elevational view of a third preferred embodiment of a facet augmentation implant according to the present invention.

Referring to FIG. 4, a third embodiment of the facet joint implant 200 includes first and second implant elements 220, 230. The third preferred embodiment of the facet joint implant 200 is similar to the second preferred embodiment of the facet joint implant 100 except in the third preferred embodiment of the facet joint implant 200, the first and second implant elements 220, 230 do not include a second end for engaging the inferior vertebral body V. Thus, the third preferred embodiment of the facet joint implant 200 engages only the superior vertebral body V. In the third preferred embodiment, the first and second implant elements 220, 230 include a cap portion 227, 237 configured to surround at least a portion of the superior articulating process of each facet joint $FJ_1$, $FJ_2$. Alternatively, it is envisioned that the first end 222, 232 of the facet joint implant 200 may be engaged to the inferior vertebral body V and the cap portion 227, 237 may surround at least a portion of the inferior articulating process of each facet joint $FJ_1$, $FJ_2$.

Accordingly, the first and second implant elements 220, 230 each include a first end 222, 232 for engaging the superior vertebral body V via one or more bone fixation elements 50 and optional eyelets 40 and a cap like end portion 227, 327 for surrounding at least a portion of the superior articulating process. At least a portion of the cap like end portion 227, 327 is disposed within the facet joints $FJ_1$, $FJ_2$.

The first and second implant elements 220, 230 are preferably made of a substantially flat, elongated anatomical strip of visco-elastic material, such as polycarbonate-urethane (PCU) or silicon that is adaptable to the posterior anatomy of the adjacent superior and inferior vertebral bodies V. The first and second implant elements 220, 230 are preferably molded to include the cap end portion 227, 237.

In operation, a bilateral pair of incisions or a single posterior incision is preferably made in a patient and the facet joint capsules are removed. Any osteophites and superflucious cartilage that are present are then removed and the facet joint spaces $FJ_1$, $FJ_2$ are cleaned and washed out. While this operation occurs, care is preferably taken to limit bleeding as much as possible, as blood tends to provoke fusion across the facet joints $FJ_1$, $FJ_2$. The cap portions 227, 237 of the first and second implant elements 220, 230 are disposed around the superior articulating process of each facet joint $FJ_1$, $FJ_2$. The first and second implant elements 220, 230 are preferably secured in a desirable position by implanting one or more bone fixation elements 50 through the first and second implant elements 220, 230 and into the adjacent vertebral bodies V, preferably in the laminar arch and/or through the pedicles. Again, the interspinous ligament is preferably spared.

Figure 5A:
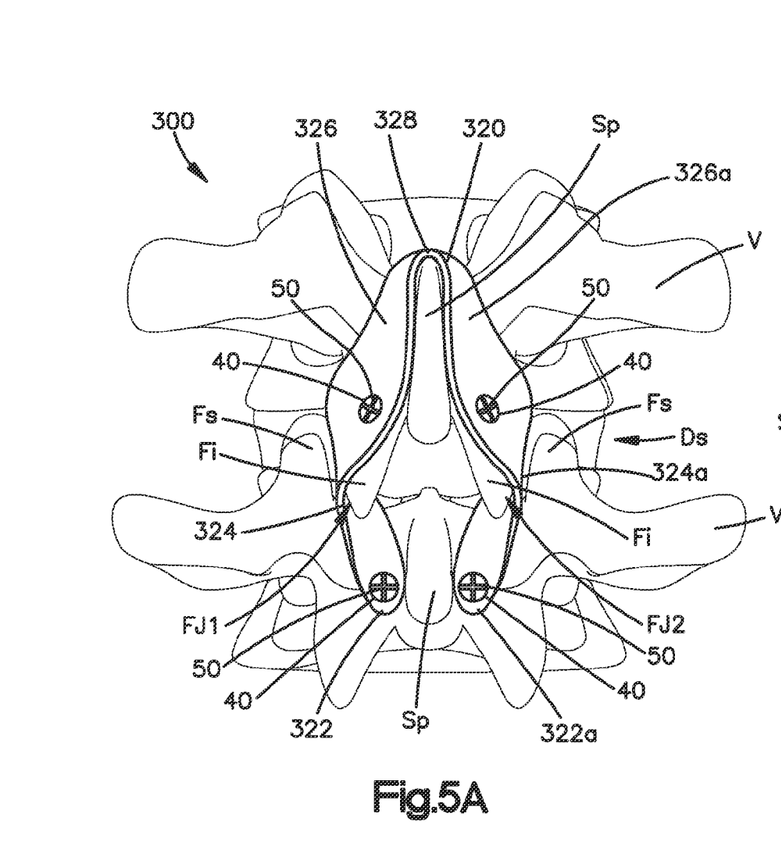
FIG. 5A illustrates a posterior elevational view of a fourth preferred embodiment of a facet augmentation implant according to the present invention.
Figure 5B:
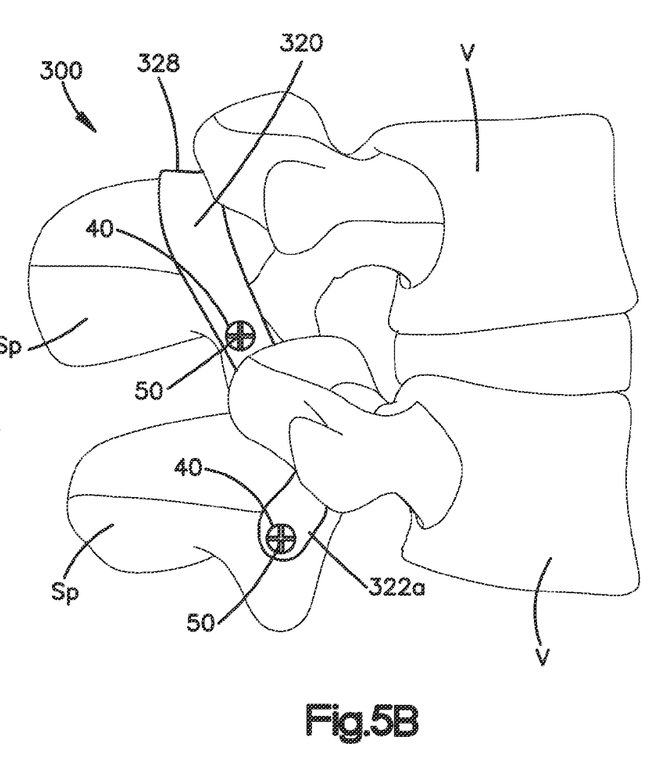
FIG. 5B illustrates a side elevational view of the facet augmentation implant shown in FIG. 5A.

Referring to FIGS. 5A and 5B, a fourth preferred embodiment of the facet joint implant 300 includes a single implant element 320. The fourth preferred embodiment of the facet joint implant 300 is similar to the first preferred embodiment of the facet joint implant 10 except in the fourth preferred embodiment of the facet joint implant 300, only a single implant element 320 is used. That is, in the fourth preferred embodiment of the facet joint implant 300, the implant element 320 preferably includes a first inferior end 322 for engaging the inferior vertebral body V by one or more bone fixation elements 50, a middle portion 324 which passes through the facet joint $FJ_1$, a first superior end 326 for engaging the superior vertebral body V via one or more bone fixation elements 50, an intermediate superior portion 328 for passing through an interspinous space, a second superior end 326a for engaging the superior vertebral body V on the opposite side of the spinous process SP via one or more bone fixation elements 50, a second middle portion 324a which passes through the facet joint $FJ_2$, and a second inferior end 322a for engaging the inferior vertebral body V by one or more bone fixation elements 50.

The implant element 320 is preferably made of a substantially flat, elongated anatomical strip of visco-elastic material, such as polycarbonate-urethane (PCU) or silicon that is adaptable to the posterior anatomy of the adjacent superior and inferior vertebral bodies V. The implant element 320 is preferably molded into anatomically fitted forms which are shaped to optimally fit between the facet joints $FJ_1$, $FJ_2$. Alternatively, as will be appreciated by one of ordinary skill in the art, the implant element 320 may be completely flat and flexible.

It should be noted that it is envisioned that a single bone fixation element (not shown) may be used to engage both the first and second superior ends 326, 326a to the superior vertebral body V. In this embodiment, the bone fixation element is inserted through the spinous process SP and through each of the first and second superior ends 326, 326a. In such an embodiment, the interior of one or both of the optional eyelets 40 may include interior threading, especially if bone screws, rivets, or pins are utilized for the bone fixation element 50. Alternatively, a single suture can also be used.

In an alternate embodiment, the first and second superior ends 326, 326a may be left unsecured to the superior vertebral body V so that the implant 320 is secured to the inferior vertebral body V only. In such an embodiment, a longer length implant is preferred and, as a result, a higher mount of flexibility and lower amount of stress is experienced across the implant.

In operation, one or more incisions are made in a patient and the strongly innervated tissue of the facet joint capsule is removed. Any osteophites and superflucious cartilage that are present are removed and the facet joint spaces $FJ_1$, $FJ_2$ are cleaned and washed out. While this operation occurs, care is preferably taken to limit bleeding as much as possible, as blood tends to provoke fusion across the facet joints $FJ_1$, $FJ_2$. A small portion of the interspinous ligament is removed and the intermediate superior portion 328 of the facet joint implant 300 is inserted into the interspinous space while the first and second middle portions 324, 324a are inserted in-between the facet joint spaces $FJ_1$, $FJ_2$, respectively. The facet joint implant 300 is then secured in place by insertion of a plurality of bone fixation elements 50 through the implant 300, preferably through respective eyelets 40. The disposition of the eyelets 40 and the bone fixation elements 50 are preferably configured to spare the pedicles.

Figure 6A:
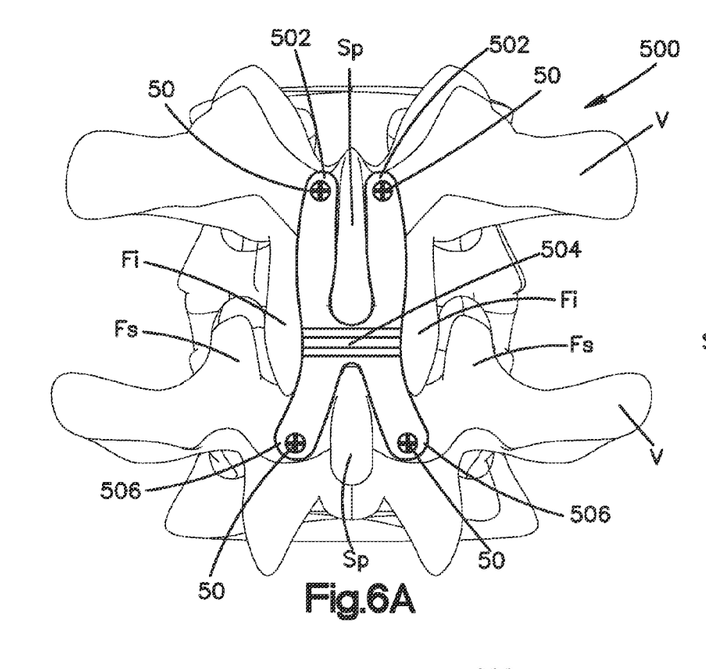
FIG. 6A illustrates a posterior elevational view of a preferred embodiment of an interspinous augmentation implant according to the present invention.
Figure 6B:
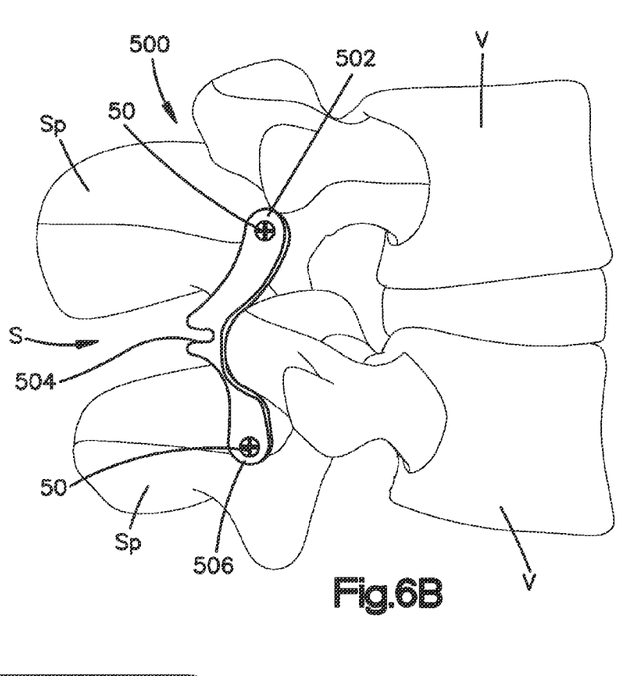
FIG. 6B illustrates a side elevational view of the interspinous implant shown in FIG. 6A.

Referring to FIGS. 6A and 6B, the concept of the present invention may also be used in connection with an interspinous spacer 500. The interspinous spacer 500 includes a first end 502 for engaging the superior vertebral body V via one or more bone fixation elements 50, a second end 506 for engaging the inferior vertebral body V via one or more bone fixation elements 50 and a middle portion 504 for passing through the interspinous space S between the adjacent vertebral bodies V in contrast to the facet joint spaces $FJ_1$, $FJ_2$ as previously described. The interspinous implant 500 is preferably anatomically molded from visco-elastic material as previously described. The middle portion 504 preferably acts as a flexible spacer, which may be in a U-shaped or W-shaped form, for flexibly maintaining the separation of the adjacent spinous processes SP.

In operation, an incision is made in the patient, the interspinous ligament is removed, and the middle portion 504 of the interspinous spacer 500 is implanted in the interspinous spacer S between adjacent spinous processes SP. The interspinous spacer 500 is preferably secured in place using a plurality of bone fixation elements 50.

Figure 7:
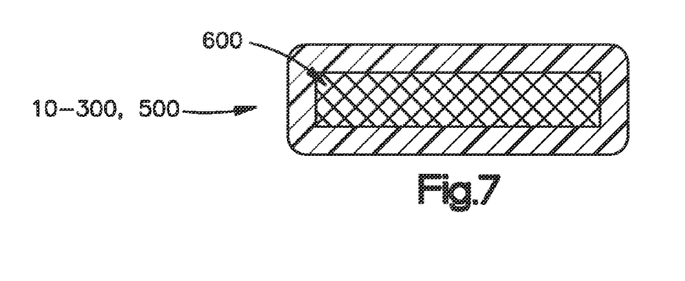
FIG. 7 illustrates an alternate cross-sectional view of the implant shown in FIGS. 2-6B, the implant incorporating a mesh-like material.

Referring to FIG. 7, the visco-elastic facet implant 10-300 of the first, second, third and fourth preferred embodiments and the interspinous spacer 500 may alternatively surround and/or encase a mesh-like material 600. More preferably, the visco-elastic material is molded around the mesh 600. In this manner, the mesh 600 acts as a stabilizing material, which serves to increase the rigidity of the implant 10-300 and 500. In addition, incorporation of the mesh 600 could, if so desired, eliminate the necessity for the eyelets 40. This way, the bone fixation elements 50 could be inserted into and through the implant 10-300 and 500 at any location on the implant 10-300 and 500 based on the patient's individual anatomy. Incorporation of the mesh 600 prevents the bone fixation elements 50 from tearing and/or ripping through the visco-elastic material. Incorporation of the mesh 600 further enables the surgeon to better tailor the implant 10-300 and 500 to the patient's individual anatomy. The mesh 600 could be constructed in any form or shape know in the art so long as it remains a mesh.

It will be appreciated by those skilled in the art that changes could be made to the preferred embodiments of the facet joint augmentation implant described above without departing from the broad inventive concept thereof. It is understood, therefore, that this invention is not limited to the particular embodiments disclosed, but it is intended to cover modifications within the spirit and scope of the present invention as defined by the present description.

The invention claimed is:

1. A facet joint implant for insertion into a facet joint between an inferior facet formed on a superior vertebral body and a superior facet formed on an inferior vertebral body, the facet implant comprising:
a first implant element including a first end for engaging the superior vertebral body via one or more bone fixation elements, a middle portion for passing through the facet joint and a second end, the implant element being manufactured from a substantially flat elongated strip of visco-elastic material that is adaptable to an anatomy of the vertebral bodies,
wherein the middle portion is configured having a substantially flat shape, wherein the middle portion includes an extension, the extension passing through the facet joint so that the first implant element may be disposed along side the facet joint in an implanted position, and such that the second end is positioned to engage the inferior vertebral body via one or more second bone fixation elements; further wherein first and second implant elements are integrally formed and include a superior portion for passing through an interspinous space.

2. The facet implant of claim 1, wherein the visco-elastic material is selected from one of a polycarbonate-urethane and silicon.

3. The facet implant of claim 1, wherein the visco-elastic implant element is injection molded into a flexible shape.

4. The facet implant of claim 1, wherein the one or more bone fixation elements are secured to a laminar arch of the superior vertebral body.

5. The facet implant of claim 1, wherein the first end includes one or more eyelets for receiving the one or more bone fixation elements.

6. The facet implant of claim 5, wherein the one or more eyelets are manufactured from a metal.

7. The facet implant of claim 5, wherein the one or more eyelets are injection molded into the first implant element.

8. The facet implant of claim 1, wherein the second end engages the inferior vertebral body via one or more bone fixation elements.

9. The facet implant of claim 8, wherein the second end includes one or more eyelets for receiving the one or more bone fixation elements.

10. The facet implant of claim 8, wherein the one or more bone fixation elements passing through the second end of the implant element are secured to a laminar arch of the inferior vertebral body.

11. The facet implant of claim 1, further comprising a second implant element for passing through a second facet joint between the adjacent superior and inferior vertebral bodies, the second facet joint being located on an opposite side of a spinous process from the first facet joint.

12. The facet implant of claim 1, wherein the middle portion and the second end are in the form of a cap for surrounding at least a portion of the inferior facet formed on the superior vertebral body.

13. A facet joint implant for insertion into first and second facet joints between a superior vertebral body and an inferior vertebral body, the first and second facet joints being located on opposite sides of a spinous process, the facet implant comprising:
a first inferior end for engaging the inferior vertebral body by one or more bone fixation elements, a middle portion for passing through the first facet joint, a first superior end for engaging the superior vertebral body, an intermediate superior portion for passing through an interspinous space, a second superior end for engaging the superior vertebral body on the opposite side of the spinous process, a second middle portion for passing through the second facet joint, and a second inferior end for engaging the inferior vertebral body by one or more bone fixation elements, the implant being manufactured from a substantially flat elongated strip of visco-elastic material that is adaptable to an anatomy of the vertebral bodies, wherein the first middle portion and the second middle portion are configured having a substantially flat shape to be passed through a respective facet joint such that the first inferior end and the second inferior end are positioned to engage the inferior vertebral body via one or more second bone fixation elements, and wherein the first and second superior ends engage the superior vertebral body via one or more bone fixation elements.

14. The facet implant of claim 13, wherein the visco-elastic material is selected from one of a polycarbonate-urethane and silicon.

15. The facet implant of claim 13, wherein the visco-elastic implant is injection molded into a flexible shape.

16. The facet implant of claim 13, wherein the one or more bone fixation elements are secured to a laminar arch of the inferior vertebral body.

17. The facet implant of claim 13, further comprising one or more eyelets for receiving the one or more bone fixation elements.

18. The facet implant of claim 17, wherein the one or more eyelets are manufactured from a metal.

19. The facet implant of claim 17, wherein the one or more eyelets are injection molded into the implant.

* * * * *